(12) United States Patent
Nakanishi et al.

(10) Patent No.: US 7,544,759 B2
(45) Date of Patent: *Jun. 9, 2009

(54) CYCLIC CARBONATE-MODIFIED ORGANOSILICON COMPOUND, NON-AQUEOUS ELECTROLYTIC SOLUTION, SECONDARY BATTERY AND CAPACITOR

(75) Inventors: Tetsuo Nakanishi, Usui-gun (JP); Meguru Kashida, Usui-gun (JP); Satoru Miyawaki, Usui-gun (JP); Shoji Ichinohe, Usui-gun (JP); Mikio Aramata, Usui-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 96 days.

This patent is subject to a terminal disclaimer.

(21) Appl. No.: 11/245,081

(22) Filed: Oct. 7, 2005

(65) Prior Publication Data

US 2006/0083992 A1   Apr. 20, 2006

(30) Foreign Application Priority Data

Oct. 15, 2004 (JP) ............................. 2004-301184
Aug. 11, 2005 (JP) ............................. 2005-233232

(51) Int. Cl.
*C08G 77/14* (2006.01)

(52) U.S. Cl. .................... 528/15; 528/26; 556/440; 429/338; 252/62.2

(58) Field of Classification Search ............ 528/15, 528/26; 556/440; 252/62.2; 429/338
See application file for complete search history.

(56) References Cited

U.S. PATENT DOCUMENTS

| | | | | |
|---|---|---|---|---|
| 3,932,464 A | * | 1/1976 | Kotzsch et al. | 549/214 |
| 4,118,540 A | * | 10/1978 | Amort et al. | 428/447 |
| 5,606,077 A | * | 2/1997 | Lersch et al. | 549/214 |
| 5,686,547 A | * | 11/1997 | Nye | 528/15 |
| 5,917,075 A | * | 6/1999 | Wolter | 556/438 |
| 6,124,062 A | | 9/2000 | Horie et al. | |
| 2004/0248014 A1 | * | 12/2004 | West et al. | 429/313 |
| 2005/0106470 A1 | * | 5/2005 | Yoon et al. | 429/324 |

FOREIGN PATENT DOCUMENTS

| | | |
|---|---|---|
| JP | 11-214032 | 8/1999 |
| JP | 2000-58123 | 2/2000 |
| JP | 2001-110455 | 4/2001 |
| JP | 2003-142157 | 5/2003 |

* cited by examiner

*Primary Examiner*—Margaret G Moore
(74) *Attorney, Agent, or Firm*—Oblon, Spivak, McClelland, Maier & Neustadt, P.C.

(57) ABSTRACT

A cyclic carbonate-modified silane or siloxane is combined with a non-aqueous solvent and an electrolyte salt to form a non-aqueous electrolytic solution, which is used to construct a secondary battery having improved temperature and high-output characteristics.

17 Claims, 4 Drawing Sheets

CYCLIC CARBONATE-MODIFIED ORGANOSILICON COMPOUND, NON-AQUEOUS ELECTROLYTIC SOLUTION, SECONDARY BATTERY AND CAPACITOR

CROSS-REFERENCE TO RELATED APPLICATION

This non-provisional application claims priority under 35 U.S.C. §119(a) on Patent Application Nos. 2004-301184 and 2005-233232 filed in Japan on Oct. 15, 2004 and Aug. 11, 2005, respectively, the entire contents of which are hereby incorporated by reference.

TECHNICAL FIELD

This invention relates to a novel organosilicon compound having a cyclic carbonate group and a non-aqueous electrolytic solution comprising the same. The non-aqueous electrolytic solution is suited for use in various energy devices, typically secondary batteries and electrochemical capacitors, typically electric double-layer capacitors, and especially lithium ion secondary batteries capable of charge/discharge operation by migration of lithium ions between positive and negative electrodes. The battery using the non-aqueous electrolytic solution of the invention has improved temperature characteristics and high-output characteristics.

BACKGROUND ART

Because of their high energy density, lithium ion secondary batteries are increasingly used in recent years as portable rechargeable power sources for laptop computers, mobile phones, digital cameras and digital video cameras. Also great efforts are devoted to the development of lithium ion secondary batteries as auxiliary power sources for electric automobiles and hybrid automobiles which are desired to reach a practically acceptable level as environment-friendly automobiles that release little or no exhaust gases to the air, or electric double-layer capacitors.

The lithium ion secondary batteries, albeit their high performance, are not satisfactory with respect to discharge characteristics in a rigorous environment, especially low-temperature environment, and discharge characteristics at high output levels requiring a large quantity of electricity within a short duration of time. On the other hand, electric double-layer capacitors suffer from problems including insufficient withstand voltage and a decline with time of electric capacity. Most such devices use non-aqueous electrolytic solutions comprising low flashpoint solvents such as dimethyl carbonate and diethyl carbonate as a main component. If thermal runaway occurs within the battery, the electrolytic solution can be evaporated and decomposed, inviting the risk of failure or ignition of the battery. This necessitates to incorporate an IC circuit in the battery as means for interrupting the current flow during anomalies and a safety valve for avoiding a rise of internal pressure within the battery due to generation of hydrocarbon gas. Further investigation on the electrolytic solution is pursued for improved safety, weight reduction and cost reduction.

Under such a situation, studies were made on polyether-modified siloxanes having high chemical stability and high compatibility with electrolytic solution. The polyether-modified siloxanes have an ability to dissolve electrolytes such as $LiPF_6$ thoroughly and due to their own surface activation capability, help wet the electrode or separator. It is also known that the addition of only several percents of polyether-modified siloxane improves charge/discharge cycle performance. These effects, however, are not sufficient. The polyether-modified siloxanes are low in thermal stability and their use at low temperature is problematic because of relatively high melting point. There is a need for additives having high safety and high compatibility with electrolytic solution.

Reference should be made to JP-A 11-214032 and JP-A 2000-58123 both corresponding to U.S. Pat. No. 6,124,062, JP-A 2001-110455, and JP-A 2003-142157.

SUMMARY OF THE INVENTION

An object of the present invention is to provide novel cyclic carbonate-modified organosilicon compounds that replace the prior art polyether-modified siloxanes. Another object is to provide a non-aqueous electrolytic solution which enables construction of a battery, especially a secondary battery, having improved discharge characteristics both at low temperatures and at high outputs and a high level of safety, and a battery, especially lithium ion secondary battery or an electrochemical capacitor such as an electric double-layer capacitor using the same.

The inventors have discovered modified silanes and siloxanes having a cyclic carbonate group as novel modified compounds that replace the prior art polyether-modified siloxanes. When a non-aqueous electrolytic solution containing the cyclic carbonate-modified silane or siloxane is used in a secondary battery or electric double-layer capacitor, the battery or capacitor is improved in charge/discharge characteristics and safety.

Specifically, the present invention provides an organosilicon compound selected from cyclic carbonate-modified silanes and siloxanes having the following general formulae (1) to (3).

Herein $R^1$ which may be the same or different is an organic group selected from among optionally halogen-substituted alkyl groups of 1 to 30 carbon atoms, aryl groups, aralkyl groups, amino-substituted alkyl groups, carboxyl-substituted alkyl groups, and alkoxy groups, a is an integer of 1 to 4, b is an integer of 0 to 3, c is an integer of 0 to 3, x and y each are 0 or 1, with the proviso that $1 \leq x+y$ when c=0, d is an integer of 0 to 5, e is an integer of 1 to 6, satisfying $3 \leq d+e \leq 6$. $R^2$ is a cyclic carbonate group having the formula (4).

The present invention also provides a non-aqueous electrolytic solution comprising as essential components a non-aqueous solvent, an electrolyte salt, and one or more organosilicon compounds selected from cyclic carbonate-modified silanes and siloxanes having the general formulae (1) to (3).

Furthermore, the present invention provides a secondary battery, electrochemical capacitor, and lithium ion secondary battery comprising the non-aqueous electrolytic solution.

The battery comprising a non-aqueous electrolytic solution containing an organosilicon compound selected from cyclic carbonate-modified silanes and siloxanes exhibits improved temperature characteristics and high-output characteristics.

DESCRIPTION OF THE PREFERRED EMBODIMENTS

The cyclic carbonate-modified organosilicon compounds of the present invention are silanes and siloxanes having the following general formulae (1) to (3).

Herein $R^1$ which may be the same or different is an alkyl group of 1 to 30 carbon atoms which may be partially substituted with halogen, aryl group, aralkyl group, amino-substituted alkyl group, carboxyl-substituted alkyl group, or alkoxy group. Examples include alkyl groups such as methyl, ethyl, propyl, butyl, pentyl, hexyl, heptyl, octyl, nonyl, and decyl; cycloalkyl groups such as cyclopentyl and cyclohexyl; aryl groups such as phenyl and tolyl; aralkyl groups such as benzyl and phenethyl; as well as amino-substituted alkyl groups such as 3-aminopropyl and 3-[(2-aminoethyl)amino]propyl and carboxy-substituted alkyl groups such as 3-carboxypropyl. Also useful are halogen atom-substituted alkyl groups, i.e., alkyl groups in which some hydrogen atoms are substituted with halogen atoms such as trifluoropropyl and nonafluorooctyl. Exemplary alkoxy groups include methoxy, ethoxy, propoxy and isopropoxy. Of these, monovalent hydrocarbon groups of 1 to 6 carbon atoms are preferred. Alkyl and fluorine-substituted alkyl groups are more preferred. Methyl or ethyl is most preferred. It is preferred that at least 80% of $R^1$ be methyl or ethyl.

$R^2$ is a cyclic carbonate group having the formula (4).

The subscript "a" is an integer of 1 to 4. In case a=3 or 4, the content of carbonate groups is relatively increased to detract from the silane or siloxane's own characteristics. For this reason, a is preferably 1 or 2. Most preferably, a is 1.

The subscripts b and c are integers satisfying $0 \leq b \leq 3$ and $0 \leq c \leq 3$. Then $0 \leq b+c \leq 6$. If the subscripts b and c representative of a degree of polymerization are greater than 3, the carbonate-modified siloxane has an increased viscosity, which can lead to a reduced ionic mobility in the electrolytic solution. Also, the carbonate-modified siloxane may become less compatible with the electrolytic solution and restrain stable dissolution of the electrolyte. It is thus preferred that b and c satisfy $0 \leq b+c \leq 3$, more preferably $0 \leq b+c \leq 2$. Each of x and y is 0 or 1, with the proviso that $1 \leq x+y$ when c=0, indicating that x+y is equal to 1 or 2. The subscripts d and e are integers satisfying $0 \leq d \leq 5$, $1 \leq e \leq 6$, and $3 \leq d+e \leq 6$. If the subscripts d and e representative of a degree of polymerization are greater than the ranges, the carbonate-modified siloxane has an increased viscosity, which can lead to a reduced ionic mobility in the electrolytic solution. Also, the carbonate-modified siloxane may become less compatible with the electrolytic solution and restrain stable dissolution of the electrolyte. It is thus preferred that d and e satisfy $0 \leq d \leq 3$ and $1 \leq e \leq 3$, more preferably $0 \leq d \leq 3$ and $1 \leq e \leq 2$.

Illustrative examples of the cyclic carbonate-modified silanes and cyclic carbonate-modified siloxanes having the general formulae (1) to (3) are given below.

The cyclic carbonate-modified silane or siloxane of the invention can be obtained through addition reaction between an organohydrogensilane or organohydrogensiloxane having a silicon-bonded hydrogen atom (SiH group) and a cyclic carbonate having a carbon-to-carbon double bond. For example, the compound of formula (ii) can be obtained through addition reaction between pentamethyldisiloxane as the SiH group-bearing siloxane and vinyl ethylene carbonate (or 4-vinyl-1,3-dioxolan-2-one).

The addition reaction is desirably effected in the presence of a platinum or rhodium catalyst. Suitable catalysts used herein include chloroplatinic acid, alcohol-modified chloroplatinic acid, and chloroplatinic acid-vinyl siloxane complexes. A co-catalyst or pH adjusting agent such as sodium acetate or sodium citrate may be added. The amount of the catalyst used is a catalytic amount, preferably up to 50 ppm, and more preferably up to 20 ppm of platinum or rhodium based on the total weight of the SiH group-containing siloxane and vinyl ethylene carbonate.

If desired, the addition reaction may be effected in an organic solvent. Suitable organic solvents include aliphatic alcohols such as methanol, ethanol, 2-propanol and butanol; aromatic hydrocarbons such as toluene and xylene; aliphatic or alicyclic hydrocarbons such as n-pentane, n-hexane, and cyclohexane; and halogenated hydrocarbons such as dichloromethane, chloroform and carbon tetrachloride. Addition reaction conditions are not particularly limited. Typically addition reaction is effected under reflux for about 1 to 10 hours.

In the other aspect, the present invention provides a non-aqueous electrolytic solution comprising the cyclic carbonate-modified organosilicon compound described above. Herein, the non-aqueous electrolytic solution contains a non-aqueous solvent and an electrolyte salt in addition to the cyclic carbonate-modified organosilicon compound.

In the non-aqueous electrolytic solution, the cyclic carbonate-modified organosilicon compound should preferably be present in an amount of at least 0.001% by volume. Less than 0.001% by volume of the organosilicon compound may not exert the desired effect. The preferred content is at least 0.1% by volume. The upper limit of the organosilicon compound content varies with a particular type of solvent used in the non-aqueous electrolytic solution, but should be determined such that migration of Li ions within the non-aqueous electrolytic solution is at or above the practically acceptable level. The organosilicon compound content is usually up to 80% by volume, preferably up to 50% by volume, and more preferably up to 50% by volume of the non-aqueous electrolytic solution. Alternatively, it is possible to eliminate a volatile solvent from the non-aqueous electrolytic solution, i.e., that the organosilicon compound content be 100% by volume of the non-aqueous electrolytic solution.

No particular limit is imposed on the viscosity of the cyclic carbonate-modified organosilicon compound. For smooth migration of Li ions within the non-aqueous electrolytic solution, the organosilicon compound should preferably have a viscosity of up to 500 mm$^2$/s, more preferably up to 100 mm$^2$/s, even more preferably up to 50 mm$^2$/s, as measured at 25° C. by a Cannon-Fenske viscometer. The lower limit of viscosity is usually at least 0.1 mm$^2$/s, though not critical.

The non-aqueous electrolytic solution of the invention further contains an electrolyte salt and a non-aqueous solvent. Typical electrolyte salts used herein are light metal salts including salts of alkali metals such as lithium, sodium and potassium, salts of alkaline earth metals such as magnesium and calcium, and aluminum salts. One or more salts may be selected for a particular purpose. Examples of lithium salts include $LiBF_4$, $LiClO_4$, $LiPF_6$, $LiAsF_6$, $CF_3SO_3Li$, $(CF_3SO_2)_2NLi$, $C_4F_9SO_3Li$, $CF_3CO_2Li$, $(CF_3CO_2)_2NLi$, $C_6F_5SO_3Li$, $C_8F_{17}SO_3Li$, $(C_2F_5SO_2)_2NLi$, $(C_4F_9SO_2)(CF_3SO_2)NLi$, $(FSO_2C_6F_4)(CF_3SO_2)NLi$, $((CF_3)_2CHOSO_2)_2NLi$, $(CF_3SO_2)_3CLi$, $(3,5-(CF_3)_2C_6F_3)_4BLi$, $LiCF_3$, $LiAlCl_4$, and $C_4BO_8Li$. These salts may be used alone or in admixture of two or more.

From the electric conductivity aspect, the electrolyte salt is preferably present in a concentration of 0.5 to 2.0 mole/liter of the non-aqueous electrolytic solution. The electrolytic solution should preferably have a conductivity of at least 0.01 S/m at 25° C., which may be adjusted by the type and concentration of the electrolyte salt.

The non-aqueous solvent used herein is not particularly limited as long as it can serve for the non-aqueous electrolytic solution. Suitable solvents include aprotic high-dielectric-constant solvents such as ethylene carbonate, propylene carbonate, butylene carbonate, and γ-butyrolactone; and aprotic low-viscosity solvents such as dimethyl carbonate, ethyl methyl carbonate, diethyl carbonate, methyl propyl carbonate, dipropyl carbonate, diethyl ether, tetrahydrofuran, 1,2-dimethoxyethane, 1,2-diethoxyethane, 1,3-dioxolane, sulfolane, methylsulfolane, acetonitrile, propionitrile, anisole, acetic acid esters such as methyl acetate, and propionic acid esters. It is desirable to use a mixture of an aprotic high-dielectric-constant solvent and an aprotic low-viscosity solvent in a proper ratio. It is also acceptable to use ionic liquids containing imidazolium, ammonium and pyridinium cations. The counter anions are not particularly limited and include $BF_4-$, $PF_6-$ and $(CF_3SO_2)_2N-$. The ionic liquid may be used in admixture with the foregoing non-aqueous solvent.

Where a solid electrolyte or gel electrolyte is desired, a silicone gel, silicone polyether gel, acrylic gel, acrylonitrile gel, poly(vinylidene fluoride) or the like may be included in a polymer form. These ingredients may be polymerized prior to or after casting. They may be used alone or in admixture.

If desired, various additives may be added to the non-aqueous electrolytic solution of the invention. Examples include an additive for improving cycle life such as vinylene carbonate, methyl vinylene carbonate, ethyl vinylene carbonate and 4-vinylethylene carbonate, an additive for preventing over-charging such as biphenyl, alkylbiphenyl, cyclohexylbenzene, t-butylbenzene, diphenyl ether, and benzofuran, and various carbonate compounds, carboxylic acid anhydrides, nitrogen- and sulfur-containing compounds for acid removal and water removal purposes.

A further embodiment of the present invention is a secondary battery comprising a positive electrode, a negative electrode, a separator, and an electrolytic solution, wherein the non-aqueous electrolytic solution described above is used as the electrolytic solution.

The positive electrode active materials include oxides and sulfides which are capable of occluding and releasing lithium ions. They may be used alone or in admixture. Examples include sulfides and oxides of metals excluding lithium such as $TiS_2$, $MoS_2$, $NbS_2$, $ZrS_2$, $VS_2$, $V_2O_5$, $MoO_3$, $Mg(V_3O_8)_2$, and lithium and lithium-containing complex oxides. Composite metals such as $NbSe_2$ are also useful. For increasing the energy density, lithium complex oxides based on $Li_pMetO_2$ are preferred wherein Met is preferably at least one element of cobalt, nickel, iron and manganese and p has a value in the range: $0.05 \leq p \leq 1.10$. Illustrative examples of the lithium complex oxides include $LiCoO_2$, $LiNiO_2$, $LiFeO_2$, and $Li_{q^-}Ni_rCo_{1-r}O_2$ (wherein q and r have values varying with the charged/discharged state of the battery and usually in the range: $0<q<1$ and $0.7<r\leq 1$) having a layer structure, $LiMn_2O_4$ having a spinel structure, and rhombic $LiMnO_2$. Also used is a substitutional spinel type manganese compound adapted for high voltage operation which is $LiMet_sMn_{1-s}O_4$ ($0<s<1$) wherein Met is titanium, chromium, iron, cobalt, nickel, copper, zinc or the like.

It is noted that the lithium complex oxide described above is prepared, for example, by grinding and mixing a carbonate, nitrate, oxide or hydroxide of lithium and a carbonate, nitrate, oxide or hydroxide of a transition metal in accordance with the desired composition, and firing at a temperature in the range of 600 to 1,000° C. in an oxygen atmosphere.

Organic materials may also be used as the positive electrode active material. Examples include polyacetylene, polypyrrole, poly-p-phenylene, polyaniline, polythiophene, polyacene, and polysulfide.

The negative electrode materials capable of occluding and releasing lithium ions include carbonaceous materials, metal elements and analogous metal elements, metal complex oxides, and polymers such as polyacetylene and polypyrrole.

Suitable carbonaceous materials are classified in terms of carbonization process, and include carbon species and synthetic graphite species synthesized by the gas phase process such as acetylene black, pyrolytic carbon and natural graphite; carbon species synthesized by the liquid phase process including cokes such as petroleum coke and pitch coke; pyrolytic carbons obtained by firing polymers, wooden materials, phenolic resins, and carbon films; and carbon species synthesized by the solid phase process such as charcoal, vitreous carbons, and carbon fibers.

Also included in the negative electrode materials capable of occluding and releasing lithium ions are metal elements and analogous metal elements capable of forming alloys with lithium, in the form of elements, alloys or compounds. Their state includes a solid solution, eutectic, and intermetallic compound, with two or more states being optionally co-present. They may be used alone or in admixture of two or more.

Examples of suitable metal elements and analogous metal elements include tin, lead, aluminum, indium, silicon, zinc, copper, cobalt, antimony, bismuth, cadmium, magnesium, boron, gallium, germanium, arsenic, selenium, tellurium, silver, hafnium, zirconium and yttrium. Inter alia, Group 4B metal elements in element, alloy or compound form are preferred. More preferred are silicon and tin or alloys or compounds thereof. They may be crystalline or amorphous.

Illustrative examples of such alloys and compounds include LiAl, AlSb, CuMgSb, $SiB_4$, $SiB_6$, $Mg_2Si$, $Mg_2Sn$, $Ni_2Si$, $TiSi_2$, $MoSi_2$, $CoSi_2$, $NiSi_2$, $CaSi_2$, $CrSi_2$, $Cu_5Si$, $FeSi_2$, $MnSi_2$, $NbSi_2$, $TaSi_2$, $VSi_2$, $WSi_2$, $ZnSi_2$, SiC, composite Si/SiC, $Si_3N_4$, $Si_2N_2O$, $SiO_v$ (wherein $0<v\leq 2$), composite SiO/C, $SnO_w$ (wherein $0<w\leq 2$), $SnSiO_3$, LiSiO and LiSnO.

Any desired method may be used in the preparation of positive and negative electrodes. Electrodes are generally prepared by adding an active material, binder, conductive agent and the like to a solvent to form a slurry, applying the slurry to a current collector sheet, drying and press bonding. The binder used herein is usually selected from polyvinylidene fluoride, polytetrafluoroethylene, styrene-butadiene rubber, isoprene rubber, and various polyimide resins. The conductive agent used herein is usually selected from carbonaceous materials such as graphite and carbon black, and metal materials such as copper and nickel. As the current collector, aluminum and aluminum alloys are usually employed for the positive electrode, and metals such as copper, stainless steel and nickel and alloys thereof employed for the negative electrode.

The separator disposed between the positive and negative electrodes is not particularly limited as long as it is stable to the electrolytic solution and holds the solution effectively. The separator is most often a porous sheet or non-woven fabric of polyolefins such as polyethylene and polypropylene. Porous glass and ceramics are employed as well.

The battery may take any desired shape. In general, the battery is of the coin type wherein electrodes and a separator, all punched into coin shape, are stacked, or of the cylinder type wherein electrode sheets and a separator are spirally wound.

The non-aqueous electrolytic solution of the invention is also applicable to electrochemical capacitors comprising electrodes, a separator, and an electrolytic solution, especially electric double-layer capacitors or pseudo-electric double-layer capacitors, asymmetrical capacitors, and redox capacitors.

At least one of the electrodes in the capacitors is a polarizable electrode composed mainly of a carbonaceous material. The polarizable electrode is generally formed of a carbonaceous material, a conductive agent, and a binder. The polarizable electrode is prepared according to the same formulation as used for the lithium secondary battery. For example, it is prepared by mixing a powder or fibrous activated carbon with the conductive agent such as carbon black or acetylene black, adding polytetrafluoroethylene as the binder, and applying or pressing the mixture to a current collector of stainless steel or aluminum. Similarly, the separator and the electrolytic solution favor highly ion permeable materials, and the materials used in the lithium secondary battery can be used substantially in the same manner. The shape may be coin, cylindrical or rectangular.

EXAMPLE

Examples of the present invention are given below for further illustrating the invention, but they are not to be construed as limiting the invention thereto. The viscosity ($mm^2/s$) is measured at 25° C. by a Cannon-Fenske viscometer.

Preparation Example 1

Synthesis of Compound Having Formula (i)

(i)

Figure 1:
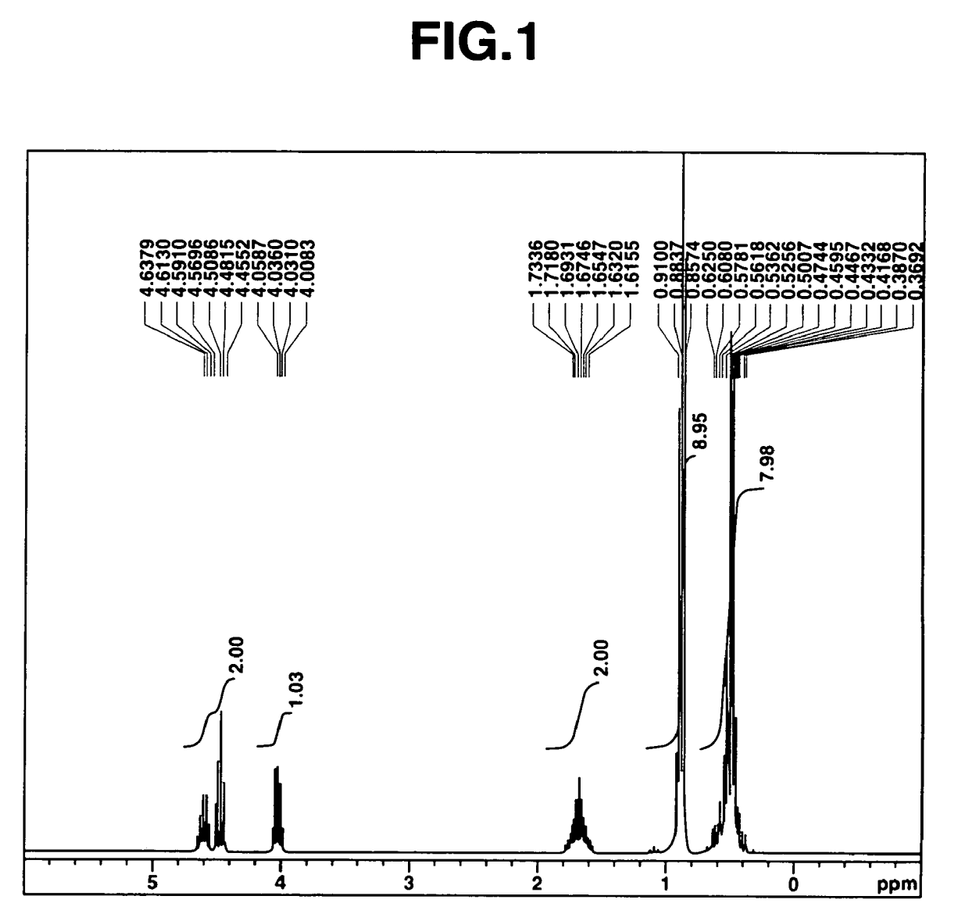
FIG. 1 is an NMR spectrum of the compound having formula (i).
Figure 2:
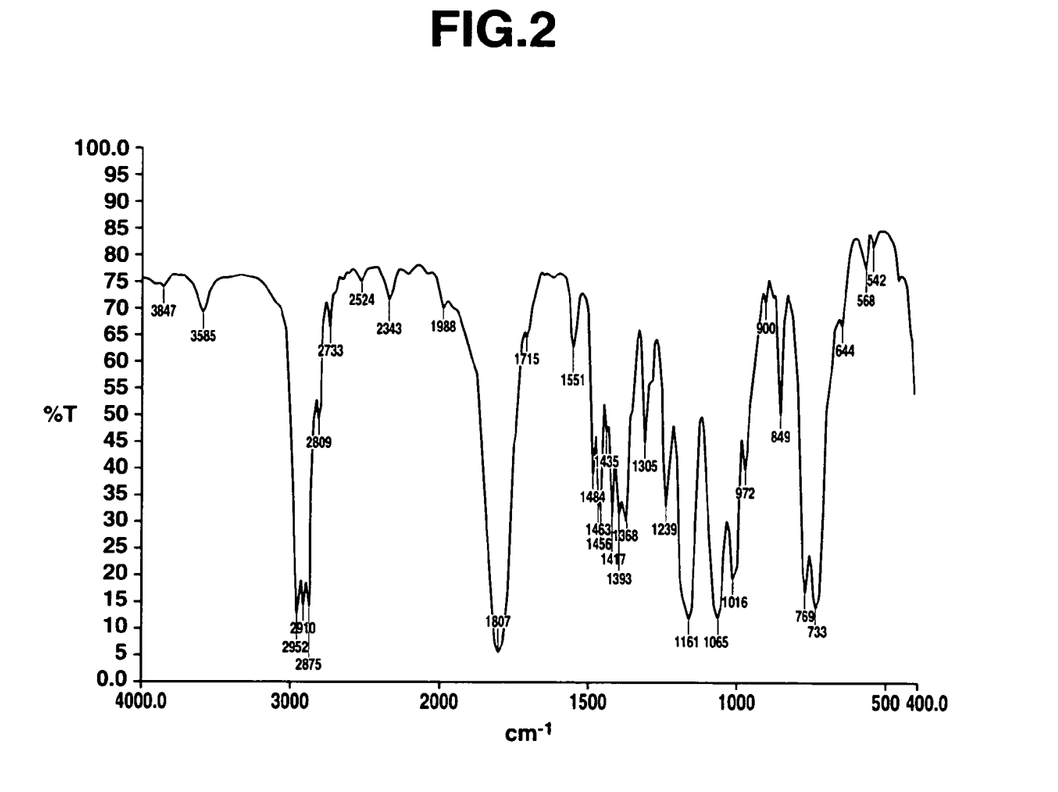
FIG. 2 is an IR absorption spectrum of the compound having formula (i).

A reactor equipped with a stirrer, thermometer and reflux condenser was charged with 103 g of vinyl ethylene carbonate, 100 g of toluene, and 0.05 g of a toluene solution of 0.5 wt% chloroplatinic acid. With stirring at 80° C., 100 g of triethylsilane was slowly added dropwise to the mixture. Reaction took place while the molar ratio of terminal unsaturated groups to SiH groups was about 1.05. After the completion of dropwise addition, the reaction solution was aged at 100° C. for 2 hours to complete the reaction. The reaction solution was precision distilled in vacuum, collecting a fraction at 148°C./7 Pa. A carbonate-modified silane having formula (i) was obtained in a yield of 49%. It had a viscosity of 17 mm$^2$/s, a specific gravity of 1.006, and a purity of 99.1% as analyzed by gas chromatography. On analysis by $^1$H-NMR using heavy chloroform as the measuring solvent, peaks appeared at 0.47 ppm (8H, m), 0.88 ppm (9H, t), 1.67 ppm (2H, m), 4.04 ppm (1H, dd), 4.48 ppm (1H, dd), and 4.61 ppm (1H, m), as seen from FIG. 1. On IR analysis, a strong signal of carbonyl group was observed at 1807 cm$^{-1}$, as seen from FIG. 2. With these data, the product was identified to be the target carbonate.

Synthesis of Compound Having Formula (ii)

(ii)

Figure 3:
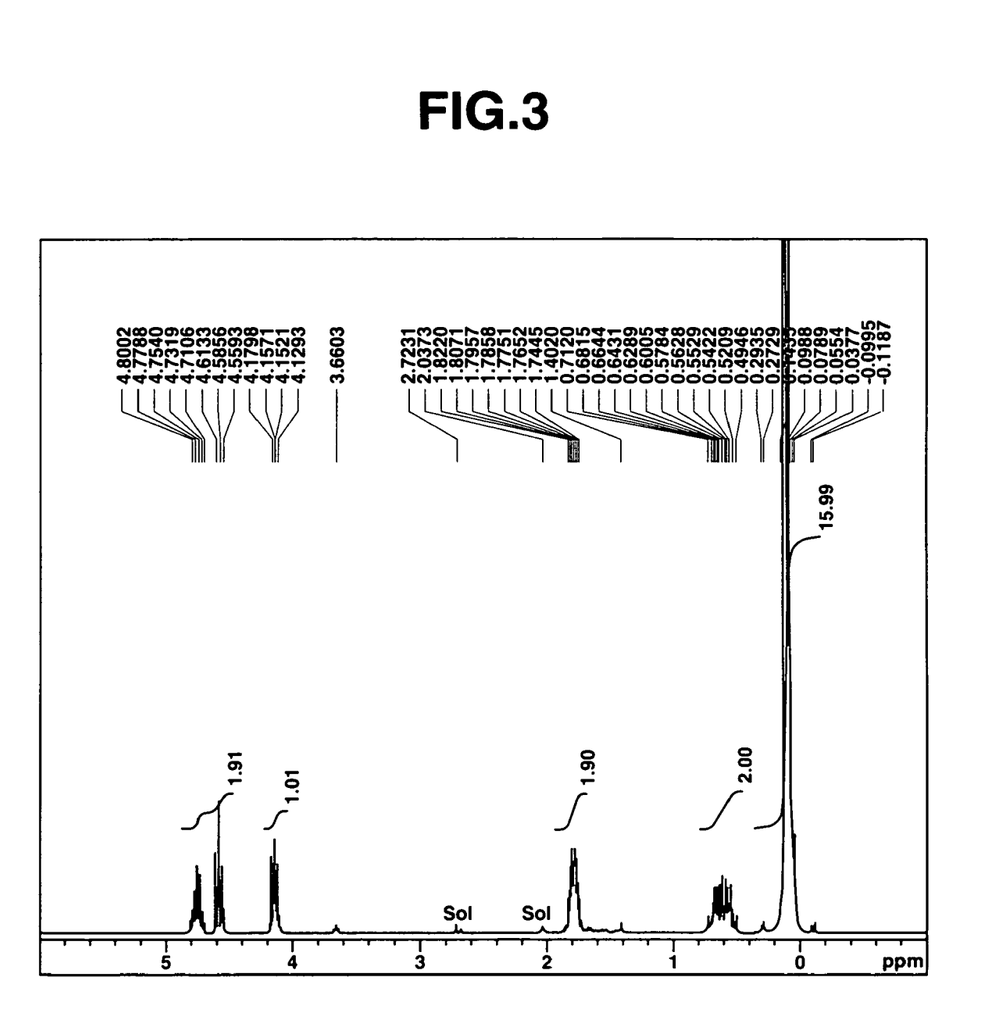
FIG. 3 is an NMR spectrum of the compound having formula (ii).
Figure 4:
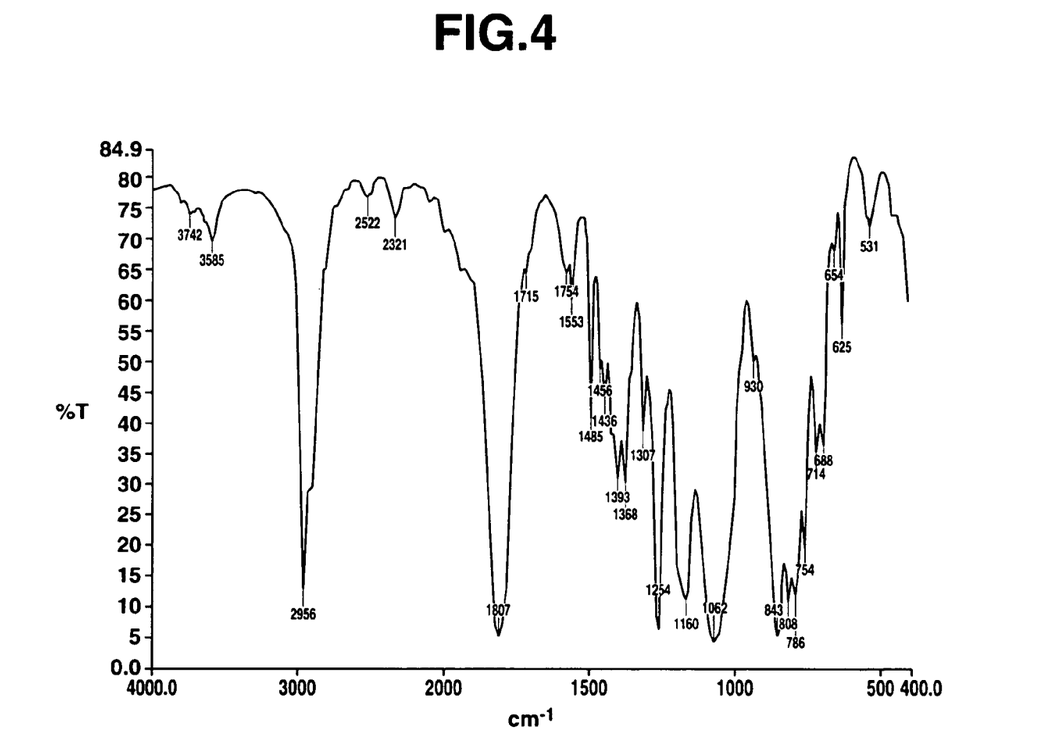
FIG. 4 is an IR absorption spectrum of the compound having formula (ii).

A reactor equipped with a stirrer, thermometer and reflux condenser was charged with 100 g of vinyl ethylene carbonate, 100 g of toluene, and 0.05 g of a toluene solution of 0.5 wt% chloroplatinic acid. With stirring at 100° C., 130 g of pentamethyldisiloxane was added dropwise to the mixture. Reaction took place while the molar ratio of terminal unsaturated groups to SiH groups was about 1.0. After the completion of dropwise addition, the reaction solution was aged at 80° C. for 2 hours to complete the reaction. The reaction solution was precision distilled in vacuum, collecting a fraction at 123°C./12 Pa. A carbonate-modified siloxane having formula (ii) was obtained in a yield of 52%. It had a viscosity of 9.3 mm$^2$/s, a specific gravity of 0.996, and a purity of 99.5% as analyzed by gas chromatography. On analysis by $^1$H-NMR using heavy acetone as the measuring solvent, peaks appeared at 0.10 ppm (15H, s), 0.55 ppm (2H, m), 1.78 ppm (2H, m), 4.15 ppm (1H, dd), 4.59 ppm (1H, dd), and 4.78 ppm (1H, m), as seen from FIG. 3. On IR analysis, a strong signal of carbonyl group was observed at 1807 cm$^{-1}$, as seen from FIG. 4. With these data, the product was identified to be the target carbonate.

Compounds having formulae (iii) to (vii) were synthesized by effecting reaction according to the same formulation as used in the synthesis of the compound having formula (ii), and using corresponding organohydrogenpolysiloxanes having a silicon-bonded hydrogen atom (SiH group).

[Preparation of Non-aqueous Electrolytic Solution]

A non-aqueous electrolytic solution was prepared by dissolving the siloxane having formula (i) to (vii) in a mixture of ethylene carbonate (EC) and diethyl carbonate (DEC) in the proportion shown in Table 1 and further dissolving LiPF$_6$ therein in a concentration of 1 mol/liter. For comparison purposes, a non-aqueous electrolytic solution free of the siloxane, and non-aqueous electrolytic solutions having 10% and 20% by volume of a polyether-modified silicone added instead were prepared.

TABLE 1

| | EC (vol %) | DEC (vol %) | Modified silane or siloxane Type | Viscosity (mm$^2$/s) | Vol % |
|---|---|---|---|---|---|
| Example 1 | 45.0 | 45.0 | i | 17 | 10 |
| Example 2 | 45.0 | 45.0 | ii | 9.3 | 10 |
| Example 3 | 40.0 | 40.0 | ii | 9.3 | 20 |
| Example 4 | 30.0 | 40.0 | ii | 9.3 | 30 |
| Example 5 | 40.0 | 40.0 | iii | 11.4 | 20 |
| Example 6 | 40.0 | 40.0 | iv | 12.8 | 20 |
| Example 7 | 45.0 | 45.0 | v | 53 | 10 |
| Example 8 | 45.0 | 45.0 | vi | 320 | 10 |
| Example 9 | 45.0 | 45.0 | vii | 216 | 10 |
| Comparative Example 1 | 50.0 | 50.0 | none | — | — |
| Comparative Example 2 | 45.0 | 45.0 | polyether-modified silicone | 100 | 10 |
| Comparative Example 3 | 40.0 | 40.0 | polyether-modified silicone | 100 | 20 |

Note that the polyether-modified silicone is described in JP-A 11-214032 and has the following formula.

[Preparation of Battery Materials]

The positive electrode material used was a single layer sheet using LiCoO$_2$ as the active material and an aluminum foil as the current collector (trade name Pioxcel C-100 by Pionics Co., Ltd.). The negative electrode material used was a single layer sheet using graphite as the active material and a copper foil as the current collector (trade name Pioxcel A-100 by Pionics Co., Ltd.). The separator used was a porous membrane of polyolefin (trade name Celgard 2400 by Celgard Co., Ltd.).

[Battery Assembly]

A battery of 2032 coin type was assembled in a dry box blanketed with argon, using the foregoing battery materials, a stainless steel can housing also serving as a positive electrode conductor, a stainless steel sealing plate also serving as a negative electrode conductor, and an insulating gasket.

[Battery Test (Low-temperature Characteristics)]

The steps of charging (up to 4.2 volts with a constant current flow of 0.6 mA) and discharging (down to 2.5 volts with a constant current flow of 0.6 mA) at 25° C. were repeated 10 cycles, after which similar charging/discharging steps were repeated at 5° C. Provided that the discharge capacity at the 10th cycle at 25° C. is 100, the number of cycles repeated until the discharge capacity at 5° C. lowered to 80 was counted.

[Battery Test (High-output Characteristics)]

The steps of charging (up to 4.2 volts with a constant current flow of 0.6 mA) and discharging (down to 2.5 volts with a constant current flow of 0.6 mA) at 25° C. were repeated 5 cycles, after which similar charging/discharging steps in which the charging conditions were kept unchanged, but the discharging current flow was increased to 5 mA were repeated 5 cycles. These two types of charging/discharging operation were alternately repeated. Provided that the discharge capacity at the 5th cycle in the initial 0.6 mA charge/discharge operation is 100, the number of cycles repeated until the discharge capacity lowered to 80 was counted.

The results are shown in Table 2.

TABLE 2

|  | Low-temperature test (cycles) | High-output test (cycles) |
| --- | --- | --- |
| Example 1 | 228 | 206 |
| Example 2 | 202 | 166 |
| Example 3 | 215 | 180 |
| Example 4 | 232 | 193 |
| Example 5 | 185 | 171 |
| Example 6 | 208 | 178 |
| Example 7 | 218 | 197 |
| Example 8 | 181 | 166 |
| Example 9 | 188 | 175 |
| Comparative Example 1 | 85 | 93 |
| Comparative Example 2 | 14 | 9 |
| Comparative Example 3 | 8 | 6 |

As seen from the results of Table 2, the batteries using carbonate-modified silanes or siloxanes within the scope of the invention manifest improved low-temperature and high-output characteristics, as compared with Comparative Example 1 not containing carbonate-modified silane or siloxane and Comparative Examples 2 and 3 using polyether-modified silicone.

Japanese Patent Application Nos. 2004-301184 and 2005-233232 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organosilicon compound selected from cyclic carbonate-modified siloxanes having the following general formula (3):

(3)

wherein $R^1$ is each independently an organic group selected from the class consisting of optionally halogen-substituted alkyl groups of 1 to 30 carbon atoms, aryl groups, aralkyl groups, amino-substituted alkyl groups, carboxyl-substituted alkyl groups, and alkoxy groups, d is an integer of 0 to 5, e is an integer of 1 to 6, satisfying $3 \leq d+e \leq 6$, and $R^2$ is a cyclic carbonate group having the formula (4):

(4)

2. A non-aqueous electrolytic solution comprising a non-aqueous solvent, 0.5 to 2.0 mol/l of an electrolyte salt, and an organosilicon compound selected from cyclic carbonate-modified silanes and siloxanes having the general formulae (1) to (3)

(1)

(2)

(3)

wherein $R^1$ is each independently an organic group selected from the class consisting of optionally halogen-substituted alkyl groups of 1 to 30 carbon atoms, aryl groups, aralkyl groups, amino-substituted alkyl groups, carboxyl-substituted alkyl groups, and alkoxy groups, a is an integer of 1 to 4, b is an integer of 0 to 3, c is an integer of 0 to 3, x and y each are 0 or 1, with the proviso that $1 \leq x+y$ when $c=0$, d is an integer of 0 to 5, e is an integer of 1 to 6, satisfying $3 \leq d+e \leq 6$, and $R^2$ is a cyclic carbonate group having the formula (4):

(4)

3. The non-aqueous electrolytic solution of claim 2 wherein in formulae (1) to (3), $R^1$ is a monovalent hydrocarbon group of 1 to 6 carbon atoms.

4. The non-aqueous electrolytic solution of claim 2 wherein the organosilicon compound is present in an amount of at least 0.001% by volume of the entire non-aqueous electrolytic solution.

5. The non-aqueous electrolytic solution of claim 2 wherein said electrolyte salt is a lithium salt.

6. A secondary battery comprising the non-aqueous electrolytic solution of claim 2.

7. An electrochemical capacitor comprising the non-aqueous electrolytic solution of claim 2.

8. A lithium ion secondary battery comprising the non-aqueous electrolytic solution of claim 2.

9. The non-aqueous electrolytic solution of claim 2 wherein said organosilicon compound is at least one selected from the group consisting of the following compounds:

10. A non-aqueous electrolytic solution comprising a non-aqueous solvent, 0.5 to 2.0 mol/l of an electrolyte salt, and an organosilicon compound having a general formula (2a):

wherein $R^1$ each independently an organic group selected from the class consisting of optionally halogen-substituted alkyl groups of 1 to 30 carbon atoms, aryl groups, aralkyl groups, amino-substituted alkyl groups, carboxyl-substituted alkyl groups, and alkoxy groups, a is an integer of 1 to 4, b is an integer of 0 to 3, c is an integer of 0 to 3, x is 0 or 1, with the proviso that x=1 when c=0, d is an integer of 0 to 5, e is an integer of 1 to 6, satisfying $3 \leq d+e \leq 6$, and $R^2$ is a cyclic carbonate group having the formula (4):

11. The non-aqueous electrolytic solution of claim 10 wherein $R^1$ is a monovalent hydrocarbon group of 1 to 6 carbon atoms.

12. The non-aqueous electrolytic solution of claim 10 wherein the organosilicon compound is present in an amount of at least 0.001% by volume of the entire non-aqueous electrolytic solution.

13. The non-aqueous electrolytic solution of claim 10 wherein said electrolyte salt is a lithium salt.

14. A secondary battery comprising the non-aqueous electrolytic solution of claim 10.

15. An electrochemical capacitor comprising the non-aqueous electrolytic solution of claim 10.

16. A lithium ion secondary battery comprising the non-aqueous electrolytic solution of claim 10.

17. A non-aqueous electrolytic solution comprising a non-aqueous solvent, 0.5 to 2.0 mol/l of an electrolyte salt and an organosilicon compound which is at least one selected from the group consisting of the following compounds:

* * * * *